United States Patent
Chen

(10) Patent No.: US 10,016,533 B2
(45) Date of Patent: *Jul. 10, 2018

(54) PLASMA MODIFIED MEDICAL DEVICES AND METHODS

(71) Applicant: Meng Chen, Columbia, MO (US)

(72) Inventor: Meng Chen, Columbia, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/457,575

(22) Filed: Mar. 13, 2017

(65) Prior Publication Data

US 2017/0296708 A1 Oct. 19, 2017

Related U.S. Application Data

(63) Continuation of application No. 14/973,401, filed on Dec. 17, 2015, now Pat. No. 9,603,978, which is a
(Continued)

(51) Int. Cl.
| | |
|---|---|
| *A61L 31/10* | (2006.01) |
| *A61L 27/34* | (2006.01) |
| *A61L 31/02* | (2006.01) |
| *A61L 31/16* | (2006.01) |
| *A61L 33/06* | (2006.01) |

(Continued)

(52) U.S. Cl.
CPC ............ *A61L 31/10* (2013.01); *A61L 31/022* (2013.01); *A61L 31/16* (2013.01); *A61L 33/0094* (2013.01); *A61L 33/068* (2013.01); *B05D 1/62* (2013.01); *A61L 2300/204* (2013.01); *A61L 2300/412* (2013.01); *A61L 2300/416* (2013.01);
(Continued)

(58) Field of Classification Search
CPC .......... A61L 31/10; A61L 27/34; A61L 27/28; B05D 1/62
USPC ...... 427/2.24, 2.25, 569, 532, 533, 535, 539
See application file for complete search history.

(56) References Cited

U.S. PATENT DOCUMENTS

| | | |
|---|---|---|
| 5,062,900 A | 11/1991 | Berneron et al. |
| 5,080,924 A | 1/1992 | Kamel et al. |

(Continued)

OTHER PUBLICATIONS

Tang et al. A study on surface endothelialization of plasma coated intravascular stents. Surface and Coatings Technology. vol. 204, Issues 9-10. pp. 1487-1492. Jan. 2010 (Year: 2010).*

(Continued)

*Primary Examiner* — Cachet I Sellman
(74) *Attorney, Agent, or Firm* — Clayton Howarth, P.C.

(57) ABSTRACT

Coatings, devices and methods are provided, wherein the contacting surface of a medical device with at least one contacting surface for contacting a bodily fluid or tissue, wherein long-lasting and durable bioactive agents or functional groups are deposited on the contacting surface through a unique two-step plasma coating process with deposition of a thin layer of plasma coating using a silicon-containing monomer in the first step and plasma surface modification using a mixture of nitrogen-containing molecules and oxygen-containing molecules in the second step. The two-step plasma coating process enables the implantable medical device to prevent both restenosis and thrombosis under clinical conditions. The invention also relates to surface treatment of metallic and polymeric biomaterials used for making of medical devices with significantly improved clinical performance and durability.

20 Claims, 3 Drawing Sheets

Related U.S. Application Data continuation of application No. 13/287,019, filed on Nov. 1, 2011, now abandoned.

(60) Provisional application No. 61/524,434, filed on Aug. 17, 2011.

(51) Int. Cl.
*A61L 33/00* (2006.01)
*B05D 1/00* (2006.01)

(52) U.S. Cl.
CPC ....... *A61L 2300/42* (2013.01); *A61L 2400/18* (2013.01); *A61L 2420/02* (2013.01)

(56) References Cited

U.S. PATENT DOCUMENTS

| | | | |
|---|---|---|---|
| 5,324,591 A | 6/1994 | Georger, Jr. et al. | |
| 5,336,518 A | 8/1994 | Narayanan et al. | |
| 5,338,770 A | 8/1994 | Winters et al. | |
| 5,449,383 A | 9/1995 | Chatelier et al. | |
| 5,463,010 A | 10/1995 | Hu et al. | |
| 5,662,960 A | 9/1997 | Hostettler et al. | |
| 5,665,077 A | 9/1997 | Rosen et al. | |
| 5,718,892 A | 2/1998 | Keefer et al. | |
| 5,770,645 A | 6/1998 | Stamler et al. | |
| 5,789,018 A | 8/1998 | Engelson et al. | |
| 5,797,887 A | 8/1998 | Rosen et al. | |
| 5,824,049 A | 10/1998 | Ragheb et al. | |
| 5,876,452 A | 3/1999 | Athanasiou et al. | |
| 5,919,570 A | 7/1999 | Hostettler et al. | |
| 5,955,588 A | 9/1999 | Tsang et al. | |
| 5,962,138 A | 10/1999 | Kolluri et al. | |
| 5,994,444 A | 11/1999 | Trescony et al. | |
| 6,017,577 A | 1/2000 | Hostettler et al. | |
| 6,087,479 A * | 7/2000 | Stamler .................. | A61K 31/00 530/363 |
| 6,168,777 B1 | 1/2001 | Greff et al. | |
| 6,218,016 B1 | 4/2001 | Tedeschi et al. | |
| 6,361,819 B1 | 3/2002 | Tedeschi et al. | |
| 6,613,432 B2 * | 9/2003 | Zamora .................. | A61L 29/08 427/2.24 |
| 7,201,935 B1 | 4/2007 | Claude et al. | |
| 7,294,357 B2 | 11/2007 | Roby | |
| 2001/0029395 A1 | 10/2001 | Stewart et al. | |
| 2003/0138645 A1 | 7/2003 | Gleason et al. | |
| 2003/0198968 A1 | 10/2003 | Matson | |
| 2004/0126596 A1 | 7/2004 | Zamora et al. | |
| 2005/0015105 A1 | 1/2005 | Tang et al. | |
| 2007/0014828 A1 * | 1/2007 | Fitzhugh ................. | A61L 27/54 424/423 |
| 2007/0281117 A1 | 12/2007 | Kaplan et al. | |
| 2011/0093056 A1 | 4/2011 | Kaplan et al. | |
| 2013/0046375 A1 | 2/2013 | Chen | |
| 2016/0184489 A1 | 6/2016 | Chen | |

OTHER PUBLICATIONS

Alfonso et al., "Intravascular ultrasound findings during episodes of drug-eluting stent thrombosis," J Am Coll Cardiol, 50: 2095-2097, 2007.
American Heart Association, "Drug-eluting stents are as safe as non-coated stents for large arteries," American Heart Association Late-Breaking Clinical Trial Report, published at www.americanheart.org, Nov. 15, 2010.
American Heart Association, "Cardiac Procedures and Surgeries At-A-Glance," published at www.americanheart.org, 2008.
Aziz et al., "Polymer stent coating for prevention of neointimal hyperplasia," J Invasive Cardiol, 18(9): 423-427, 2006.
Basalus et al., "Scanning electron microscopic assessment of the biodegradable coating on expanded biolimus-eluting stents," EuroIntervention, 5(4): 505-10, 2009.
Byrne et al., "Polymer coatings and delayed arterial healing following drug-eluting stent implantation," Minerva Cardioangiol, 57(5): 567-584, 2009.
Chen et al., "NH3/O2 mixed gas plasmas alter the interaction of blood components with stainless steel," J Biomed Mater Res, 67A: 994-1000, 2003.
Chilkoti et al., "Investigating the relationship between surface chemistry and endothelial cell growth: partial least-squares regression of the static secondary ion mass spectra of oxygen-containing plasma-deposited films," Anal Chem, 67: 2883-2891, 1995.
Chin-Quee et al., "Endothelial cell recovery, acute thombogenicity, and monocyte adhesion and activation on Fluorinated copolymer and phosphorylcholine polymer stent coatings," Biomaterials, 31(4): 648-657, 2010.
Chu et al., "Plasma-surface modification of biomaterials," Mater Sci Eng, R36: 143-206, 2002.
Costa et al., "Preliminary results of the hydroxyapatite nonpolymer-based sirolimus-eluting stent for the treatment of single de novo coronary lesions a first-in-human analysis of a third-generation drug-eluting stent system," JACC Cardiovasc Interv, 1(5): 545-551, 2008.
Daemen et al., "Early and late coronary stent thrombosis of sirolimus-eluting and paclitaxel-eluting stents in routine clinical practice: data from a large two-institutional cohort study," Lancet. 369: 667-678, 2007.
Ertel et al., "Endothelial cell growth on oxygen-containing films deposited by radio-frequency plasmas: the role of surface carbonyl groups," J Biomater Sci Polym Ed, 3:163-183, 1991.
Ertel et al., "Radiofrequency plasma deposition of oxygen-containing films on polystyrene and poly(ethylene terephthalate) substrates improves endothelial cell growth," J Biomed Mater Res, 24: 1637-1659, 1990.
Fine et al., "Enhanced endothelial cell functions on rosette nanotube-coated titanium vascular stents," Int J Nanomedicine, 4:91-97, 2009.
Fontaine et al., "Decreased platelet adherence of polymer-coated tantalum stents," J Vasc Intery Radiol, 5: 567-572, 1994.
Fontaine et al., "Polymeric surface modifications of tantalum stents," J Endovasc Sur, 3: 276-283, 1996.
Gotman, "Characteristics of metals used in implants," J Endourol, 11: 383-389, 1997.
Griesser et al., "Growth of human cells on plasma polymers: putative role of amine and amide groups," J Biomater Sci Polym Ed, 5: 531-554, 1994.
Grube et al., "BioMatrix Bioliums A9-eluting cornary stent: a next-generation drug-eluting stent for coronary artery disease," Expert Rev Med Devices, 3(6): 731-741, 2006.
Harsch et al., "Pulsed plasma deposition of allylamine on polysiloxane: a stable surface for neuronal cell adhesion," J Neurosci Methods, 98: 135-144, 2000.
Huang et al., "The short-term effect on resenosis and thrombosis of a cobalt-chromium stent eluting two drugs in a porcine coronary artery model," J Interv Cariol, 22(5): 466-478, 2009.
Indolfi et al., The present and future of drug-eluting stens. Ital Heart J., 6(6): 498-506, 2005.
Joner et al., "Pathology of drug-eluting stents in humans; delayed healing the late thrombotic risk," J Am Coll Cardiol, 48: 193-202, 2006.
Kotani et al., "Incomplete neointimal coverage of sirolimus-eluting stents," J Am Coll Cardiol, 47: 2108-2111, 2006.
Lerouge et al., "Nitrogen-rich coatings for promoting healing around stent-grafts after endovascular aneurysm repair," Biomaterials, 28(6): 1209-1217, 2007.
Lin et al., "In situ endothelialization of intravascular stents coated with an anti-CD34 antibody functionalized heparin-collagen multilayer," Biomaterials, 31(14): 4017-4025, 2010.
Liu et al., Increased osteoblast functions among nanophase titania/poly(lactide-co-glycolide) composites of the highest nanometer surface roughness, J Biomed Mater Res A, 78A(4): 798-807, 2006.
Lockwood et al., "In vitro and in vivo characterization of novel biodegradable polymers for application as drug-eluting stent coatings," Biomater Sci Polym Ed, 21(4): 529-552, 2010.

(56) References Cited

OTHER PUBLICATIONS

Maalej et al., "The potent platelet inhibitory effects of S-nitrosated albumin coating of artificial surfaces," J Am Coll Caridol, 33(5): 1408-1414, 1999.

Mooradian et al., "Effect of glow discharge surface modification of plasma TFE vascular graft material on fibronectin and laminin retention and endothelial cell adhesion," J Surg Res, 53: 74-81, 1992.

Orbusneich, "OrbusNeich Expands Global Sales and Marketing Team," published at www.orbusneich.com/genous/ (2007), accessed Jul. 2008.

Pendyala et al., "Passive and active polymer coatings for intracoronary stents: novel devices to promote arterial healing," J Interv Cardio, 22(1): 37-48, 2009.

Ramires et al., "Plasma-treated PET surfaces improve the biocompatability of human endothelial cells," J Biomed Mater Res, 51: 535-539, 2000.

Ratner, "Biomaterials Science: Overview and Opportunities with Special Reference to Organic and Polymeric Glow Discharge Plasma Treatments," in Plasma Processing of Polymers (D'Agostino et al.), Academic Publishers, Dordrecht, The Netherlands, 1997.

Roger et al., "Heart Disease and Stroke Statistics—2012 Update: A Report from the American Heart Association," published at www.americanheart.org, Dec. 15, 2011.

Steele et al., "Roles of serum vitronectin and fibronectin in initial attachment of human vein endothelial cells and dermal fibroblasts on oxygen- and nitrogen-containing surfaces made by radiofrequency plasmas," J Biomater Sci Polym Ed, 6: 511-532, 1994.

Tang et al. A study on surface endothelialization of plasma coated intravascular stents. Surface and Coating Technology. vol. 204, Issues 9-10. pp. 1487-1492. Jan. 2010.

Tepe et al., "Reduced thrombogenicity of nitinol stents—in vitro evaluation of different surface modifications and coatings," Biomaterials, 27(4): 643-650, 2006.

Tharp et al., "Local Delivery of the KCa3.1 Blocker, TRAM-34, Prevents Acute Angioplasty-Induced Coronary Smooth Muscle Phenotypic Modulation and Limits Stenosis," Arterioscler Thromb Vasc Biol, 28(6): 1084-1089, 2008.

Tseng et al., "Effects of amide and amine plasma-treated ePTFE vascular grafts on endothelial cell lining in an artificial circulatory system" J Biomed Mater Res, 42: 188-198, 1998.

Tsujino et al., "Drug delivery via nano-, micro- and macroporous coronary stent surfaces," Expert Opin Drug Deliv, 4 (3): 287-295, 2007.

Van Der Giessen et al., "Marked inflammatory sequelae to implantation of biodegradable and nonbiodegradable polymers in porcine cornary arteries," Circulation, 94: 1690-1697, 1996.

Wessely, "New drug-eluting stent concepts," Nat Rev Cardiol, 7(4): 194-203, 2010.

Zamora et al., "Radiolabelling brachytherapy sources with Re-188 trough chelating microfilms: stents," J Biomed Mater Res (Appl Biomater), 53: 244-251, 2000.

Zhou et al., "Preparation and characterization of polymeric coatings with combined nitric oxide release and immobilized active heparin," Biomaterials, 26: 6506-6517, 2005.

\* cited by examiner

PLASMA MODIFIED MEDICAL DEVICES AND METHODS

CROSS-REFERENCE TO RELATED APPLICATIONS

This application is a continuation of U.S. application Ser. No. 14/973,401, filed Dec. 17, 2015, now U.S. Pat. No. 9,603,978, which is a continuation of U.S. application Ser. No. 13/287,019, filed Nov. 1, 2011, which claims the benefit of U.S. Provisional Application No. 61/524,434, filed Aug. 17, 2011, all of which are hereby incorporated by reference herein in their entireties, including but not limited to those portions that specifically appear hereinafter, the incorporation by reference being made with the following exception: In the event that any portion of the above-referenced applications is inconsistent with this application, this application supersedes the above-referenced applications.

STATEMENT REGARDING FEDERALLY SPONSORED RESEARCH AND DEVELOPMENT

This invention was made with government support under grant No. 1R44HL097485-01A2 from the National Institutes of Health. The government has certain rights in the invention.

FIELD OF THE INVENTION

This invention relates to applications and methods for glow discharge plasma coatings for medical devices with improved long-term biocompatibility for clinical practice. Particularly, the present invention relates implantable medical devices such as stents, catheters, pacemakers, and biosensors, and the like, wherein long-lasting and durable bioactive agents or functional groups are deposited on the device surface through a unique two-step plasma coating process to prevent both restenosis and thrombosis in clinical conditions. The invention also relates to surface treatment of metallic and polymeric biomaterials used for making of medical devices with significantly improved clinical performance and durability.

BACKGROUND OF THE INVENTION

Note that the following discussion refers to a number of publications by author(s) and year of publication, and that due to recent publication dates certain publications are not to be considered as prior art to the present invention. Discussion of such publications herein is given for more complete background and is not to be construed as an admission that such publications are prior art for patentability determination purposes.

Coronary heart disease (CHD) caused by atherosclerosis, the narrowing of the coronary arteries due to fatty build up of plaque, remains a major healthcare problem in the US. Each year about 450,000 Americans die of CHD, and approximately 1.26 million Americans have a new or recurrent coronary event. CHD is the leading cause of death in the United States [Cardiovascular disease statistics www.americanheart.org/]. In clinical practice, a coronary artery stent, a small mesh tube made of metal or alloys, functions as a scaffold to prop open blocked arteries in the heart to keep them from re-narrowing (referred to clinically as restenosis). However, about 25% of implanted bare metal stents (BMS) still experience restenosis (typically at six-months). In contrast, drug-eluting stents (DES) have reduced the rate of restenosis to <10%, when used for clinically approved indications.

However, concerns were raised in recent years about the safety of DES due to a reportedly small but significantly increased risk of blood clots in the stent within 1 year after stenting (i.e. stent thrombosis). In fact, after DES implantation, late stent thrombosis (i.e. defined as occurring 1-12 months after percutaneous coronary intervention, PCI) occurs in 0.5% of patients, and the risk of very late stent thrombosis (i.e. occurring >1 year after PCI) remains elevated for at least 4 years post stenting [Daemen J, et al.: Lancet. 369: 667-678, 2007]. While not frequent, late stent thrombosis is a life-threatening problem. Delayed healing is considered a leading cause of late stent thrombosis, which has been confirmed by intravascular ultrasound [Alfonso et al. J Am Coll Cardiol. 50: 2095-2097, 2007] and angioscopic studies [Kotani et al. J Am Coll Cardiol. 47: 2108-2111, 2006]. Each year about 600,000 Americans are getting DES [Stent facts. http://americanheart.mediaroom.com/], which means that even a small increased risk could result in thousands of heart attacks and deaths. Furthermore, the requirement for prolonged, aggressive anti-thrombotic therapy after placement of a DES (usually aspirin and clopidogrel) can introduce major complications into the management of patients who require surgical procedures (which necessitate temporary discontinuation of anti-thrombotic drugs) within the first year after PCI.

When compared to coronary bypass graft surgery for restoring blood flow, coronary angioplasty, where inflation of a small balloon in the blocked artery restores blood flow, is a less expensive clinical procedure. Every year about 1.31 million angioplasties through PCI are performed in the US [Angioplasty and Cardiac Revascularization Statistics. www.americanheart.org/]. Restenosis following angioplasty, however, is a major clinical problem since the biological response to this vessel damage is stimulation of accelerated growth of arterial smooth muscle cells. The use of BMS to reduce restenosis rate after angioplasty has revolutionized the field of interventional cardiology [Indolfi et al. Ital Heart J, 6(6): 498-506, 2005]. DES while allowing controlled release of a drug directly to the injured artery for decreased restenosis, have caused late stent thrombosis, which is thought to be attributed to the continuous elution of drugs, leaving a layer of polymer on the surface of stents. The polymer coating may trigger chronic inflammation and hypersensitivity reactions in some patients [Pendyala et al. J Interv Cardio, 22(1): 37-48, 2009]. Autopsy studies indicated that the lack of complete endothelial coverage of stent struts associated with persistence of fibrin deposits, is the primary pathoanatomic substrate of late stent thrombosis after DES implantation [Joner et al. J Am Coll Cardiol. 48: 193-202, 2006; Byrne et al. Minerva Cardioangiol, 57(5): 567-584, 2009]. This delayed healing was not found in patients with BMS.

Therefore, there is a need for coatings and surfaces of medical devices that prevent restenosis and thrombosis, particularly for coronary artery stents for improved safety and efficacy with their use in patients with coronary heart disease.

A variety of methods have been developed for improved biocompatibility of implanted stents. A new drug delivery technology, using a porous stent surface [Tsujino et al. Expert Opin Drug Deliv, 4(3): 287-295, 2007], may offer desirable drug elution properties. However, it is still at an early stage. Biodegradable polymers are being explored as a new platform for DES [Grube et al. Expert Rev Med Devices, 3(6): 731-741, 2006; Lockwood et al. *Biomater Sci Polym Ed*, 21(4): 529-552, 2010], but further investigation for clinical use is needed, and recent morphology studies of biodegradable coatings have shown cracks in the coatings after stent expansion [Basalus et al. *EuroIntervention*. 5(4): 505-10, 2009]. The performance and efficacy of the polymer-free vestasync-eluting stent (VES) have been investigated recently [Costa et al. *JACC Cardiovasc Interv.* 1(5): 545-551, 2008], but a long term follow-up with a more complex subset of patients and lesions is required to confirm their preliminary results. A novel polymer coating adsorbed to stent surfaces was revealed to reduce neointimal hyperplasia in a 6 week porcine restenosis model [Billinger et al. *J Invasive Cardiol*, 18(9): 423-427, 2006], but whether or not it will develop late thrombosis in stent is an unanswered question. Polyurethane coating has been applied to stents and found to inhibit platelet attachment [Fontaine et al. *J Vasc Interv Radiol*, 5: 567-572, 1994; Fontaine et al. *J Endovasc Sur*, 3: 276-283, 1996] and reduce thrombogenicity [Tepe et al. *Biomaterials*, 27(4): 643-650, 2006]. However, long-term implantation of polyurethane-coated stents has also been found to induce chronic inflammation [van de Giessen et al. *Circulation*, 94: 1690-1697, 1996]. A new dual acting polymeric coating that combines NO (nitric oxide) release with surface-bound heparin was developed to prevent thrombosis to mimic the nonthrombogenic properties of the endothelial cell layer that lines the inner wall of healthy blood vessels [Zhou et al. *Biomaterials*, 26: 6506-6517, 2005]. However, no systematical study for stent application has been reported. Another approach is to attach radioactive material to the stent surface to prevent restenosis [Zamora et al. *J Biomed Mater Res (Appl Biomater)*, 53: 244-251, 2000], but the polyurethane used as a sealant for the radioactive agent on the stent surface remains problematic in causing chronic inflammation. A new biomimetic nanostructured coating (no drugs) on titanium was reported to significantly increase endothelial cell density, but further exploration is needed for stent application [Fine et al. *Int J Nanomedicine*. 4:91-97, 2009]. In summary, none of those aforementioned approaches addresses both issues of late thrombosis and in-stent restenosis with one specific coating. It has been noted that Orbus Neich promotes its coating to both prevent thrombosis and lower the risk of restenosis. The coating process consists of three steps including a surface priming process, bio-chemical reaction, and covalent bonding [Orbus Neich Expands Global Sales and Marketing Team. www.orbusneich.com/genous/]. The use of two drugs coated on stents to simultaneously minimize both restenosis and thrombosis has been studied recently [Huang et al. *J Interv Cardiol*, 22 (5): 466-478, 2009]. The animal studies showed a significant reduction in restenosis, but whether or not the late stent thrombosis will develop remains unclear.

In recent years, plasma processes have been widely used in the preparation of biomedical materials with unique performance and in the manufacturing of medical devices [Ratner BD in: *Plasma Processing of Polymers*, 1997]. For instance, a new nitrogen-rich plasma-deposited biomaterial as an external coating for stent-grafts can promote healing around the implant after endovascular aneurysm repair [Lerouge et al. *Biomaterials*, 28(6):1209-1217, 2007]. Plasma deposition is a thin film forming process typically occurring in a vacuum chamber, where thin films deposit on the surface of substrates under plasma conditions. In a plasma deposition process, monomers are introduced into a plasma reactor and get activated to produce a gaseous complex composed of highly energetic electrons, ions, free radicals and excited monomer molecules, known as the plasma state. Through plasma deposition, many appropriate functional groups, such as amine, hydroxyl, carboxylic acid, useful for the immobilization of bioactive molecules, can be created in the deposited coatings. More importantly, these chemical groups can be put onto almost any material by choosing right monomers and plasma process parameters.

Plasma surface treatment has also become a powerful tool in solving surface preparation problems on biomedical materials [Chu et al. *Mater Sci Eng*, R36: 143-206, 2002]. Oxygen plasmas, for example, have been used to increase the attachment of cells to polymer surfaces [Ertel et al. *J Biomater Sci Polym Ed*, 3:163-183, 1991; Chilkoti et al. *Anal Chem*, 67: 2883-2891, 1995; Ertel et al. *J Biomed Mater Res*, 24: 1637-1659, 1990]. Plasmas have also been used to introduce amines and amides to polymeric materials for increasing the attachment of cells, and in particular endothelial cells [Griesser et al. *J Biomater Sci Polym Ed*, 5: 531-554, 1994; Ramires et al. *J Biomed Mater Res*, 51: 535-539, 2000; Tseng et al. *J Biomed Mater Res*, 42: 188-198, 1998; Harsch et al. *J Neurosci Methods*, 98: 135-144, 2000]. Absorption of two blood proteins, fibronectin and vitronectin, is also modified by plasma treatment [Mooradian et al. *J Surg Res*, 53: 74-81, 1992; Steele et al. *J Biomater Sci Polym Ed*, 6: 511-532, 1994], and that directly influences endothelial cell attachment. In addition to polymers, surfaces of metals like stainless steel and titanium, which are widely used in the construction of medical devices [Gotman *J Endourol*, 11: 383-389, 1997], have also been treated with plasmas for a variety of purposes.

U.S. Pat. No. 6,613,432, provides a method of using plasma surface modification to introduce a bioactive layer or coating on the surface of implantable medical devices for improved biocompatibility, such as inhibition of restenosis with stents and attachment of platelets and leukocytes. However, in large animal studies with this patented plasma technology, certain, often large variations have been observed on the patency of plasma treated stents after implantation, which is believed to be due to the potential instability of surface bioactivity generated by the single-step $NH_3/O_2$ plasma surface treatment on bare stainless steel surfaces.

As discussed above, the currently available coronary stents and the methods under development for improved biocompatibility of stents have the following crucial problems: 1) existing stent procedures with BMS still experience a high incidence of restenosis; 2) although DES, in comparison with BMS, have been much more widely used due to their better ability in controlling restenosis carry the risk of developing late stent thrombosis, which is associated with a clinically significant risk of mortality; and 3) most existing coating processes investigated have the major limitation of being incapable of preventing restenosis and thrombosis at the same time. Thus it would be desirable to provide new coatings for surfaces of medical devices that exhibit both reduced restenosis and thrombosis. In particular, it would be desirable to provide methods for preparing and fabricating devices and substrates to prevent these problems from happening.

REFERENCES

1. Cardiovascular disease statistics. www.americanheart.org/ (accessed August 2011).
2. Daemen J, Wenaweser P, Tsuchida K, et al.: Early and late coronary stent thrombosis of sirolimus-eluting and paclitaxel-eluting stents in routine clinical practice: data from a large two-institutional cohort study. *Lancet.* 369: 667-678, 2007.
3. Alfonso F, Suárez A, Pérez-Vizcayno M J, et al.: Intravascular ultrasound findings during episodes of drug-eluting stent thrombosis. *J Am Coll Cardiol.* 50: 2095-2097, 2007.
4. Kotani J, Awata M, Nanto S, et al.: Incomplete neointimal coverage of sirolimus-eluting stents. *J Am Coll Cardiol.* 47: 2108-2111, 2006.
5. Stent facts. http://americanheart.mediaroom.com/ (accessed August 2011).
6. Angioplasty and Cardiac Revascularization Statistics. www.americanheart.org/ (accessed August 2011).
7. Indolfi C, Mongiardo A, Spaccarotella C, et al.: The present and future of drug-eluting stents. *Ital Heart J,* 6(6): 498-506, 2005.
8. Pendyala L, Jabara R, Robinson K, Chronos N: Passive and active polymer coatings for intracoronary stents: novel devices to promote arterial healing. *J Interv Cardio,* 22(1): 37-48, 2009.
9. Joner M, Finn A V, Farb A, et al.: Pathology of drug-eluting stents in humans: delayed healing and late thrombotic risk. *J Am Coll Cardiol.* 48: 193-202, 2006.
10. Byrne R A, Joner M, Kastrati A: Polymer coatings and delayed arterial healing following drug-eluting stent implantation. *Minerva Cardioangiol,* 57(5): 567-584, 2009.
11. Tsujino I, Ako J, Honda Y, et al.: Drug delivery via nano-, micro and macroporous coronary stent surfaces. *Expert Opin Drug Deliv,* 4(3): 287-295, 2007.
12. Grube E and Buellesfeld L.: BioMatrix Biolimus A9-eluting coronary stent: a next-generation drug-eluting stent for coronary artery disease. *Expert Rev Med Devices,* 3(6): 731-741, 2006.
13. Lockwood N A, Hergenrother R W, Patrick L M, Stucke S M, Steendam R, Pacheco E, Virmani R, Kolodgie F D, Hubbard B: In vitro and in vivo characterization of novel biodegradable polymers for application as drug-eluting stent coatings. *Biomater Sci Polym Ed,* 21(4): 529-552, 2010.
14. Basalus M W, van Houwelingen K G, Ankone M, de Man F H, von Birgelen C: Scanning electron microscopic assessment of the biodegradable coating on expanded biolimus-eluting stents. *EuroIntervention.* 5(4): 505-10, 2009.
15. Costa J R Jr, Abizaid A, Costa R, et al.: Preliminary results of the hydroxyapatite nonpolymer-based sirolimus-eluting stent for the treatment of single de novo coronary lesions a first-in-human analysis of a third-generation drug-eluting stent system. *JACC Cardiovasc Interv.* 1(5): 545-551, 2008.
16. Billinger M, Buddeberg F, Hubbell J A, et al.: Polymer stent coating for prevention of neointimal hyperplasia. *J Invasive Cardiol,* 18(9): 423-427, 2006.
17. Fontaine A B, Koelling K, Clay J, et al.: Decreased platlet adherence of polymer-coated tantalum stents. *J Vasc Interv Radiol,* 5: 567-572, 1994.
18. Fontaine A B, Koelling K, Passos S D, et al.: Polymeric surface modifications of tantalum stents. *J Endovasc Sur,* 3: 276-283, 1996.
19. Tepe G, Schmehl J, Wendel H P, et al.: Reduced thrombogenicity of nitinol stents—in vitro evaluation of different surface modifications and coatings. *Biomaterials,* 27(4): 643-650, 2006.
20. van de Giessen W J, Lincoff A M, Schwartz R S, et al.: Marked inflammatory sequelae to implantation of biodegradable and nonbiodegradable polymers in porcine coronary arteries. *Circulation,* 94: 1690-1697, 1996.
21. Zhou Z R and Meyerhoff M E: Preparation and characterization of polymeric coatings with combined nitric oxide release and immobilized active heparin. *Biomaterials,* 26: 6506-6517, 2005.
22. Zamora P O, Osaki S., Som P, et al.: Radiolabelling brachytherapy sources with Re-188 trough chelating microfilms: stents. *J Biomed Mater Res (Appl Biomater),* 53: 244-251, 2000.
23. Fine E, Zhang L, Fenniri H and Webster T J: Enhanced endothelial cell functions on rosette nanotube-coated titanium vascular stents. *Int J Nanomedicine.* 4:91-97, 2009.
24. Orbus Neich Expands Global Sales and Marketing Team. www.orbusneich.com/genous/. 2007 (accessed July 2008).
25. Huang Y, Venkatraman S S, Boey F Y C, Umashankar P R, Mohanty M, and Arumugam S: The short-term effect on restenosis and thrombosis of a cobalt-chromium stent eluting two drugs in a porcine coronary artery model. *J Interv Cardiol,* 22 (5): 466-478, 2009,
26. Ratner B D in: *Plasma Processing of Polymers.* d'Agostino R, Favia P and Fracassi F, Ed. Kluwer Academic Publishers, Dordrecht, The Netherlands, 1997.
27. Lerouge S, Major A, Girault-Lauriault P L, et al.: Nitrogen-rich coatings for promoting healing around stent-grafts after endovascular aneurysm repair. *Biomaterials,* 28(6):1209-1217, 2007.
28. Chu P K, Chen J Y, Wang L P, et al.: Plasma-surface modification of biomaterials. *Mater Sci Eng, R*36: 143-206, 2002.
29. Ertel S I, Chilkoti A., Horbett T A, et al.: Endothelial cell growth on oxygen-containing films deposited by radiofrequency plasmas: the role of surface carbonyl groups. *J Biomater Sci Polym Ed,* 3:163-183, 1991.
30. Chilkoti A., Schmierer A E, Perez-Luna V H, et al.: Investigating the relationship between surface chemistry and endothelial cell growth: partial least-squares regression of the static secondary ion mass spectra of oxygen-containing plasma-deposited films. *Anal Chem,* 67: 2883-2891, 1995.
31. Ertel S I, Ratner B D and Horbett T A.: Radiofrequency plasma deposition of oxygen-containing films on polystyrene and poly(ethylene terephthalate) substrates improves endothelial cell growth. *J Biomed Mater Res,* 24: 1637-1659, 1990.
32. Griesser H J, Chatelier R C, Gengenbach T R, et al.: Growth of human cells on plasma polymers: putative role of amine and amide groups. *J Biomater Sci Polym Ed,* 5: 531-554, 1994.
33. Ramires P A., Mirenghi L., Romano A R, et al.: Plasma-treated PET surfaces improve the biocompatibility of human endothelial cells. *J Biomed Mater Res,* 51: 535-539, 2000.
34. Tseng D Y and Edelman E R: Effects of amide and amine plasma-treated ePTFE vascular grafts on endothelial cell lining in an artificial circulatory system. *J Biomed Mater Res,* 42: 188-198, 1998.
35. Harsch A, Calderon J, Timmons R B, et al.: Pulsed plasma deposition of allylamine on polysiloxane: a stable surface for neuronal cell adhesion. *J Neurosci Methods,* 98: 135-144, 2000.
36. Mooradian D L., Trescony P, Keeney K., et al.: Effect of glow discharge surface modification of plasma TFE vascular graft material on fibronectin and laminin retention and endothelial cell adhesion. *J Surg Res,* 53: 74-81, 1992.

37. Steele J G, Johnson G, McFarland C, et al.: Roles of serum vitronectin and fibronectin in initial attachment of human vein endothelial cells and dermal fibroblasts on oxygen- and nitrogen-containing surfaces made by radiofrequency plasmas. *J Biomater Sci Polym Ed*, 6: 511-532, 1994.

38. Gotman I: Characteristics of metals used in implants. *J Endourol*, 11: 383-389, 1997.

39. Zamora P O, Osaki S and Chen M: Plasma-deposited coatings, devices and methods. U.S. Pat. No. 6,613,432, Sep. 2, 2003.

40. Lin Q, Ding X, Qiu F, Song X, Fu G, Ji J: In situ endothelialization of intravascular stents coated with an anti-CD34 antibody functionalized heparin-collagen multilayer. *Biomaterials*, 31(14): 4017-4025, 2010.

41. Wessely R: New drug-eluting stent concepts. *Nat Rev Cardiol*, 7(4):194-203, 2010.

42. Maalej N, Albrecht R, Loscalzo J and Folts J D: The potent platelet inhibitory effects of S-nitrosated albumin coating of artificial surfaces. *J Am Coll Cardiol*. 33 (5): 1408-1414, 1999.

43. Chen M, Zamora P O, Som P, et al.: $NH_3/O_2$ mixed gas plasmas alter the Interaction of blood components with stainless steel. *J Biomed Mater Res*, 67A: 994-1000, 2003.

44. Chin-Quee S L, Hsu S H, Nguyen-Ehrenreich K L, Tai J T, Abraham G M, Pacetti S D, Chan Y F, Nakazawa G, Kolodgie F D, Virmani R, Ding N N, Coleman L A: Endothelial cell recovery, acute thrombogenicity, and monocyte adhesion and activation on fluorinated copolymer and phosphorylcholine polymer stent coatings. *Biomaterials*, 31(4): 648-657, 2010.

45. Liu H, Slamovich E, Webster T: Increased osteoblast functions among nanophase titania/poly(lactide-co-glycolide) composites of the highest nanometer surface roughness. *J. Biomed Mater Res A*, 78 A (4): 798-807, 2006.

46. Tharp D L, Wamhoff B R, Wulff H, Raman G, Cheong A and Bowles D K: Local Delivery of the KCa3.1 Blocker, TRAM-34, Prevents Acute Angioplasty-Induced Coronary Smooth Muscle Phenotypic Modulation and Limits Stenosis. *Arterioscler Thromb Vasc Biol*, 28(6): 1084-1089, 2008.

BRIEF SUMMARY OF THE INVENTION

The invention provides an implantable medical device having at least one contacting surface for contacting a bodily fluid or tissue, wherein the contacting surface is coated by a two step process of plasma treatment comprising a first step of a plasma deposition process using silicon-containing monomers to provide a uniform and conformal nano-scale plasma coating and a second step of a plasma modification process using a mixture of nitrogen and oxygen molecules. In one embodiment, the nitrogen-containing molecules each comprise no more than six atoms, and preferably four or fewer atoms. The nitrogen-containing molecules may include $NH_3$, $NH_4$, $N_2O$, $NO$, $NO_2$ and $N_2O_4$. The oxygen-containing molecules may include $O_2$ and $O_3$. The plasma treatment with the nitrogen-containing molecules and the oxygen-containing molecules may be simultaneous.

It is a feature of an illustrative embodiment of the present invention to provide a novel biocompatible coating of high thrombo-resistance on the surface of metallic biomaterials of which coronary stents are made. As an environmentally benign technology, a low temperature plasma process is invented to deposit an ultra-thin (nano-scale) but continuous layer of coating, sufficient to generate the desired abrasion resistance and immobilize the bioactive functional groups created in the subsequent plasma surface treatment to prevent blood clots and restenosis, but thin enough to allow for stent expansion without cracking when delivered into patients. The plasma modified metallic surfaces exhibit the following properties: 1) non-clot formation on the $NH_3/O_2$ plasma treated stainless steel (SS) surface, combined with increased apoptosis in smooth muscle cells (SMC), and non-inflammatory responses; 2) a thin trimethylsilane (TMS) coating followed by $NH_3/O_2$ plasma surface modification with direct current (DC) plasma which delivers statistically significant increases in coronary artery endothelial cell (EC) attachment without promoting SMC proliferation on SS wafers at 12 weeks after plasma coating, suggesting formations of stable and durable bioactive surfaces; 3) a stainless steel stent coated with the two-step plasma coating with DC plasma which exhibits significantly less intimal hyperplasia than untreated controls in swine arteries; 4) surface bound NO functional groups which play a role similar to free NO in inhibiting fibrinogen adsorption and preventing platelet aggregation; and 5) a preferred plasma coating in thickness of 20 nm which shows robust adhesion to SS substrates and no coating cracks observed after stent expansion. In addition to application to coronary stents, the significantly improved biocompatibility for medical devices can also be employed for other implantable medical devices such as pacemakers, pulse generators, cardiac defibrillators and bio-sensors, etc.

The plasma treatment is for less than about five minutes, preferably for less than about two minutes, more preferably for less than about one minute, and most preferably for between about thirty seconds and about one minute.

In one embodiment, the nitrogen-containing molecules are $NH_3$ and the oxygen-containing molecules are $O_2$. The mass flow rate during plasma treatment with each of $NH_3$ and of $O_2$ is between a ratio of about 1.5:1 and about 1:1.5. In an alternative embodiment, the nitrogen-containing molecules are $N_2O$ and the oxygen-containing molecules are $O_2$. The mass flow rate during plasma treatment with each of $N_2O$ and of $O_2$ is between a ratio of about 1.5:1 and about 1:1.5.

The medical devices of this invention include stents, catheters, balloons, shunts, valves, pacemakers, pulse generators, cardiac defibrillators, spinal stimulators, brain stimulators, sacral nerve stimulators, leads, inducers, sensors, seeds, screws, anchors, plates and joints. The at least one contacting surface may be a metallic material, or may be a polymeric material. If it is a polymeric material, it may be biodegradable.

The device can further include a biologically compatible coating deposited over the two-step plasma coating process. In one embodiment, the biologically compatible coating may be a polymer or co-polymer, such as poly acrylate, poly bisphenol A carbonate, polybutadiene, polycarbonate, poly butylene terephthalate, poly butyl methachyalate, polydimethyl siloxane, polyester, polyethyleneimine, poly methyl methachrylate, polypropylene, polystyrene, polysulfone, polyurethane, poly vinyl, poly vinyl acetate polylactide, polyglycolide, polycaprolactone, or polyvinylidine fluoride.

The invention further consists of a coating for an implantable medical device with at least one contacting surface for contacting a bodily fluid or tissue, which coating includes a first layer on the contacting surface that includes the product of the two step plasma coating process.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be constituted as limiting the invention. In the drawings.

DETAILED DESCRIPTION

Figure 1:
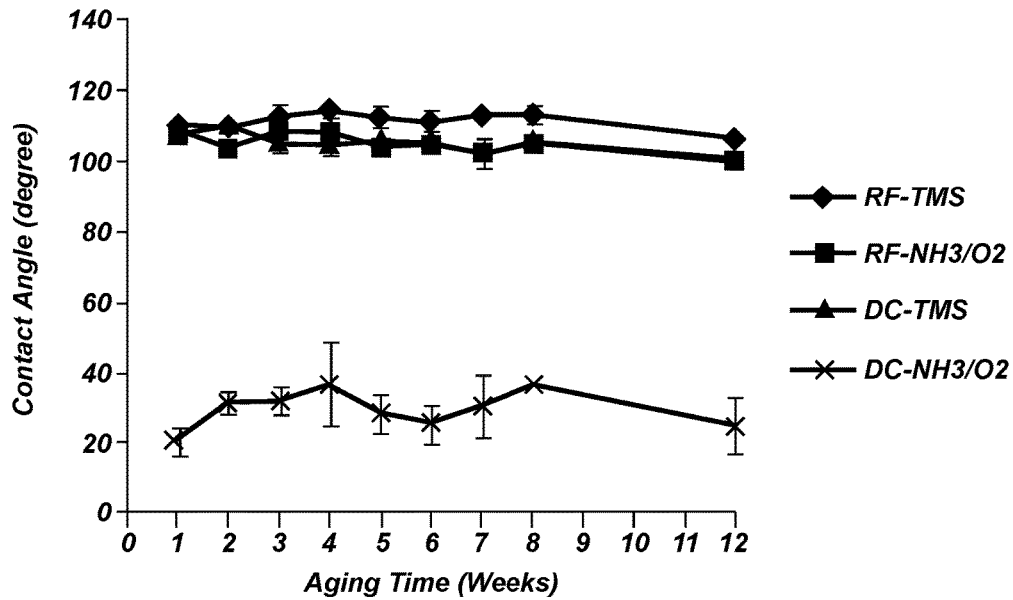
FIG. 1 Water contact angle of plasma coated stainless steel (SS) wafers using direct current (DC) and radiofrequency (RF) plasmas vs. aging time. DC-TMS: SS coated with TMS (Trimethylsilane) coating using DC plasma; DC-NH$_3$/O$_2$: SS coated with TMS coating followed by NH$_3$/O$_2$ treatment using DC plasma; RF-TMS: SS coated with TMS coating using RF plasma; RF-NH$_3$/O$_2$: SS coated with TMS coating followed by NH$_3$/O$_2$ treatment using RF plasma. For Bare SS (uncoated) wafers, contact angle: 77°±3° (not shown in the Figure). Data are means±standard deviations for n=4.

Before the present plasma modified medical devices and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Unless defined otherwise, all technical and scientific terms used herein have the same meanings as commonly understood by one of ordinary skill in the art to which this invention belongs. In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

The invention provides an implantable medical device with a plasma-modified surface, which medical device has at least one contacting surface for contacting a bodily fluid or tissue, wherein the contacting surface is modified by deposition of a thin layer of plasma coating and a subsequent plasma surface modification with nitrogen-containing molecules and oxygen-containing molecules. In the device, the plasma-modified contacting surface exhibits significantly enhanced adhesion of endothelial cells, compared to a similar surface that is not plasma modified with the method provided in this invention, suggesting rapid endothelialization on plasma-modified implantable medical devices.

The invention comprises a structural component having at least one plasma-modified contacting surface with resultant desirable or medically-useful properties.

Suitable structural components with a contacting surface include medical devices that are intended to contact blood or other tissues, such as stents, catheters, shunts, grafts, and other medical devices known in the art. The structural component may include a mesh, coil, wire, inflatable balloon, or any other device or structure which is capable of being implanted at a target location, including intravascular target locations, intraluminal target locations, target locations within solid tissue, such as for the treatment of tumors, and the like.

The implantable device can be intended for permanent or temporary implantation. Such devices may be delivered by or incorporated into intravascular and other medical catheters. Suitable surfaces include stainless steel, nitinol, titanium, other metal alloys, polyvinyl chloride, polyethylene, polylactide, poly glycolide, poly caprolactone, poly methyl methacrylate, poly hydroxylethyl methacrylate, polyurethane, polystyrene, polycarbonate, dacron, extended poly tetrafluoroethylene (Teflon®), related fluoropolymer composites (Gore-Tex®), or combinations thereof. All or part of the available surface can be modified. Other substrate materials can also be used, including poly acrylate, poly bisphenol A carbonate, polybutadiene, poly butylene terephthalate, poly butryl methacrylate, polydimethyl siloxane, polyester, polyethyleneimine, polysulfone, poly vinyl acetate, polyvinylidine fluoride, polylactide, poly glycolide, poly caprolactone and copolymers and variants thereof.

A suitable method of exposing the structural components with a surface to the plasma involves placement of the structural components in a plasma field singly, in groups, or by methods involving fluidized bed or the like, which is disclosed in U.S. Pat. No. 6,613,432, and hereby incorporated by reference.

The present invention provides a nano-scale (less than 100 nm) plasma coating that is fabricated by a glow discharge plasma deposition process for an implantable medical device made of metals or alloys or polymers with at least one contacting surface for contacting a bodily fluid or tissue, and followed by plasma surface modification using a mixture of oxygen-containing molecules and nitrogen-containing molecules to create bioactive functional groups such as nitric oxide or oxynitrites on the surface.

This two-step plasma process is performed using two different plasma sources including radio-frequency (RF) and direct current (DC) without taking the wafers or stents out of plasma reactor between the two steps. Silicon-containing monomers are used for thin coating deposition. This type of organosilanes can be polymerized and deposited rapidly onto the substrate surface with good adhesion through a glow discharge plasma coating process.

The organosilanes usable for this purpose, which can be employed singly or in any combination, include trimethylsilane (TMS), vinyltrichlorosilane, tetraethoxysilane, vinyltriethoxysilane, hexamethyldisilazane, tetramethylsilane, vinyldimethylethoxysilane, vinyltrimethoxysilane, tetravinylsilane, vinyltriacetoxysilane, and methyltrimethoxysilane. In one embodiment, the silicon-containing monomers comprise organosilanes that are gases under normal conditions: i.e. 0-25° C. and 1-2 atm. In another embodiment, the silicon-containing monomers comprise a member selected from the organosilanes that can be vaporized at a temperature of less than 100° C. In yet another embodiment, the silicon-containing monomers comprise a member selected from the silane group consisting of $(CH_3)_3$—SiH and $(CH_3)_2$—SiH$_2$. In yet another embodiment, the silicon-containing monomers comprise trimethylsilane (TMS). Plasma deposited organosilicon coatings exhibit not only as dense a film as conventional plasma coatings do, but also provides a certain degree of abrasion-resistance for the stent surface due to its inorganic —Si—Si— and —Si—C—Si— backbone. The good adhesion is attributed to the formation of a chemical bond between the plasma-deposited layer and the surface of metals or polymers. When the first step of plasma deposition process is completed, the resulting nano-scale (less than 100 nm) plasma coating is treated by a second plasma treatment using a mixture of nitrogen and oxygen molecules. In one embodiment, a mixture of $NH_3/O_2$ is used for plasma surface treatment because these gases will be activated by the highly energetic electrons produced in the plasma chamber to form nitric oxide on the surface thereby providing long-lasting bioactivity to the surface which promotes endothelialization on the medical device surface, for example, stent struts. The second steps of plasma treatment using a $NH_3/O_2$ gas mixture provides the desired oxynitrite functional groups with a maximized amount attached onto the plasma coating surface, also through covalent bonding. The combination of the two-step processed plasma coatings of the present invention provides a stable and durable functionalized surface and consequently results in significantly improved performance of the plasma coated implantable devices. The functional and durable plasma coatings provided in this invention with two-step processes prove very cost-effective by creating bioactive agents on stent surfaces that inhibit both restenosis and in-stent thrombosis without using any drugs or reagents. Non-drug-based stent coatings are considered a novel approach to improve the safety and efficacy of stents [Wessely et al. *Nat Rev Cardiol,* 7(4):194-203, 2010].

The structural components as used herein refer to virtually any device that can be temporarily or permanently implanted into or on a human or animal host. Suitable structural components with a surface include those that are intended to contact blood including stents, catheters, shunts, grafts, and the like. Suitable devices that are intended as tissue implanted include brachytherapy sources, embolization materials, tumor-bed implants, intra-joint implants, materials to minimize adhesions, and the like. The device may include a mesh, coil, wire, inflatable balloon, bead, sheet, or any other structure which is capable of being implanted at a target location, including intravascular target locations, intraluminal target locations, target locations within solid tissue, typically for the treatment of tumors, and the like. The implantable device can be intended for permanent or temporary implantation. Such devices may be delivered by or incorporated into intravascular and other medical catheters. The device can be implanted for a variety of purposes, including tumor treatment, treatment or prophylaxis of cardiovascular disease, the treatment of inflammation, reduction of adhesions, and the like. In one application, the device is used for treatment of hyperplasia in blood vessels which have been treated by conventional recanalization techniques, particularly intravascular recanalization techniques, such as angioplasty, atherectomy, and the like.

Exemplary structural components and devices include intravascular stents. Intravascular stents include both balloon-expandable stents and self-expanding stents. Balloon-expandable stents are available from a number of commercial suppliers, including from Cordis under the Palmaz-Schatz tradename. Self-expanding stents are typically composed from a shape memory alloy and are available from suppliers, such as Instent. In the case of stents, a balloon-expandable stent is typically composed of a stainless steel framework or, in the case of self-expanding stents, from nickel/titanium alloy. Both such structural frameworks are suitable for use in this invention.

Exemplary devices also include balloons, such as the balloon on balloon catheters. The construction of intravascular balloon catheters is well known and amply described in the patent and medical literature. The inflatable balloon may be a non-dispensable balloon, typically being composed of polyethyleneterephthalate, or may be an elastic balloon, typically being composed of latex or silicone rubber. Both these structural materials are suitable for coating according to the methods of this invention.

The implantable devices will have one or more surfaces or a portion of a surface that is treated with gas plasma composed of molecular species containing oxygen and nitrogen. In the case of stents it is particularly desirable to treat the entire surface. In the case of balloons mounted on catheters it is desirable to coat at least the outer cylindrical surface of the balloon that will be in contact with the blood vessel when the balloon is inflated therein.

In addition to the described devices, a variety of other implantable structures, such as wires, coils, sheets, pellets, particles, and nanoparticles, and the like, may be treated with the gas plasma containing molecular species composed of oxygen and nitrogen according to the methods of the present invention. This includes tissue-implanted brachytherapy sources, embolization materials, tumor-bed implants and the like.

The devices may be introduced to the patient in a conventional manner, depending on the device. In the case of stents, a stent delivery catheter, typically an intravascular balloon catheter in the case of balloon-expanded stents or a containment catheter in the case of self-expanding stents.

The invention is thought to be particularly useful as applied to cardiovascular stents and for the prevention of restenosis following stent placement, and other interventional treatments, but may also be used in other therapies, such as tumor treatment or in controlling inflammation or thrombosis. Any device in accord with the invention would typically be packaged in a conventional medical device package, such as a box, pouch, tray, tube, or the like. The instructions for use may be printed on a separate sheet of paper, or may be partly or entirely printed on the device package. The implantable device within the package may optionally be sterilized.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

Example 1: Preparation of Stents

Stainless steel coronary artery stents when unexpanded had dimensions of 1.6 mm (diameter)×12 mm (length) with a total exposed wire surface area of 20.66 mm². The stents were cleaned with a 2% (v/v) Detergent 8 solution for 30 min at 50° C. in an ultrasonic bath. The stents were then sonicated in distilled water for 30 min at 50° C. Stents were given a final rinse with distilled water and dried in an oven at 50° C. for 30 min.

The stents were then threaded through an electrically conductive metal wire that had been attached to aluminum panels with a surface area 15.3 cm×7.6 cm, using silver epoxy. For DC treatment groups, we used an oxygen pretreatment step (1 sccm oxygen, 50 mTorr, 20 W DC, 2 min) followed by TMS plasma polymer deposition (1 sccm TMS, 50 mTorr, 5 W DC, 15 s) and a 2:1 ammonia/oxygen plasma surface modification treatment for 2 min at 50 mTorr and 5 W DC. For RF treatment groups, we used an oxygen pretreatment step (1 sccm oxygen, 50 mTorr, 20 W RF, 2 min) followed by TMS plasma polymer deposition (1 sccm TMS, 50 mTorr, 30 W RF, 4 min) and a 2:1 ammonia/oxygen plasma surface modification for 2 min at 50 mTorr and 5 W RF.

Example 2: Water Contact Angle of Plasma Coated Stainless Steel Wafers

Measurements were taken on plasma coated wafers for up to 12 weeks following the plasma coating to evaluate the long term stability. The results indicated the plasma coated surfaces tend to stabilize at about two weeks after plasma processing, and the wafers coated with TMS followed by $NH_3/O_2$ plasma treatment using DC plasma (FIG. 1) remained very hydrophilic at 12 weeks after the plasma coating process as compared to uncoated controls, indicating long-lasting surface bioactivity generated by the plasma coating process.

Example 3: Plasma Coating Adhesion to Substrate Surface and Coating Integrity

A cross-hatch was made using a razor blade on plasma coated stainless steel wafers followed by a Scotch® tape pull test. Visual inspection showed that there was no coating coming off the cross-hatched or its surrounding area, indicative of strong adhesion to the underlying surface, which warrants the coating integrity when flexed during stent crimping, navigation and expansion in clinical application.

Stainless steel stents of generic design in the dimension of Ø1.6 mm×12 mm (diameter×length) before dilation were used for the coating cracking test. After plasma coatings, the stents were imaged using an optical microscope at 20× and 50× magnifications. Following imaging, the samples were expanded with a balloon catheter (monorail' Maverick PTCA Dilatation Catheter, Boston Scientific, Natick Mass.) and inflated to 3.0 mm in diameter; the stents were then visualized again via optical microscopy and Scanning Electron Microscopy (SEM) to determine if the expansion created any cracks on the plasma coatings. Our microscopic examinations summarized in Table 1 demonstrated that expansion of stents did not cause any cracks on plasma coatings with thickness of 20 nm.

Table 1 Microscopic examination of plasma coatings on stent after expansion

TABLE 1

Microscopic examination of plasma coatings on stent after expansion

| Method of microscopy | DC plasma coating | | RF plasma coating | |
| --- | --- | --- | --- | --- |
| | thickness of 20 nm | 100 nm | thickness of 20 nm | 100 nm |
| Optical (50x) | No cracks | cracks | No cracks | cracks |
| SEM (600x) | No cracks | | No cracks | |

Example 4: Surface Chemistry Analysis

DC plasma coated SS wafers were analyzed with X-ray Photoelectron Spectroscopy (XPS) and the results are presented in Table 2. It is shown that the elemental composition of both N and O was increased at the surface with TMS coating followed by $NH_3/O_2$ plasma surface modification, indicative of oxynitrites or NO (nitric oxide) functional groups formed on the surface. The stability of these NO groups on the surface was evidenced by the similar level of N and O on the 1 and 4 weeks old wafers after plasma treatment. The analysis of high resolution spectrum for N(1s) also indicated NO formation.

Those NO functionalities can be durably maintained since they are covalently bonded to the plasma coated surface. It has been reported in the literature [Maalej et al. *J Am Coll Cardiol.* 33 (5): 1408-1414, 1999] that NO-coated surfaces are more resistant to binding of thrombogenic molecules such as fibrinogen. Fibrinogen and other serum proteins will bind to damaged endothelial surfaces or stent surfaces before platelet and mediate platelet adhesion and aggregation. Our previous studies also indicated that the nitrosated SS surface using $NH_3/O_2$ plasma surface modification (no plasma coating deposition prior to $NH_3/O_2$ plasma treatment) had an inhibitory effect on the binding of fibrinogen [Chen et al. *J Biomed Mater Res*, 67A: 994-1000, 2003]. These results implied that plasma coatings with surface bound NO functional groups inhibit binding of pro-thrombotic molecules before platelet aggregation, playing an important role similar to free NO in preventing thrombosis.

TABLE 2

Surface composition as determined by XPS

| Plasma treatment | C | Si | O | N | Si/C | O/C | N/C |
| --- | --- | --- | --- | --- | --- | --- | --- |
| 1 week | TMS(DC) | 46.62 | 39.03 | 14.1 | 0.25 | 0.837 | 0.302 | 0.005 |
| | TMS + NH3/O2(DC) | 14.51 | 42.45 | 41.27 | 1.77 | 2.926 | 2.844 | 0.122 |
| 4 weeks | TMS(DC) | 44.85 | 38.44 | 16.61 | 0.11 | 0.857 | 0.370 | 0.002 |
| | TMS + NH3/O2(DC) | 17.29 | 34.93 | 45.47 | 2.32 | 2.020 | 2.630 | 0.134 |

Example 5: Endothelialization of Plasma Coated Stainless Steel Wafers

Figure 2:
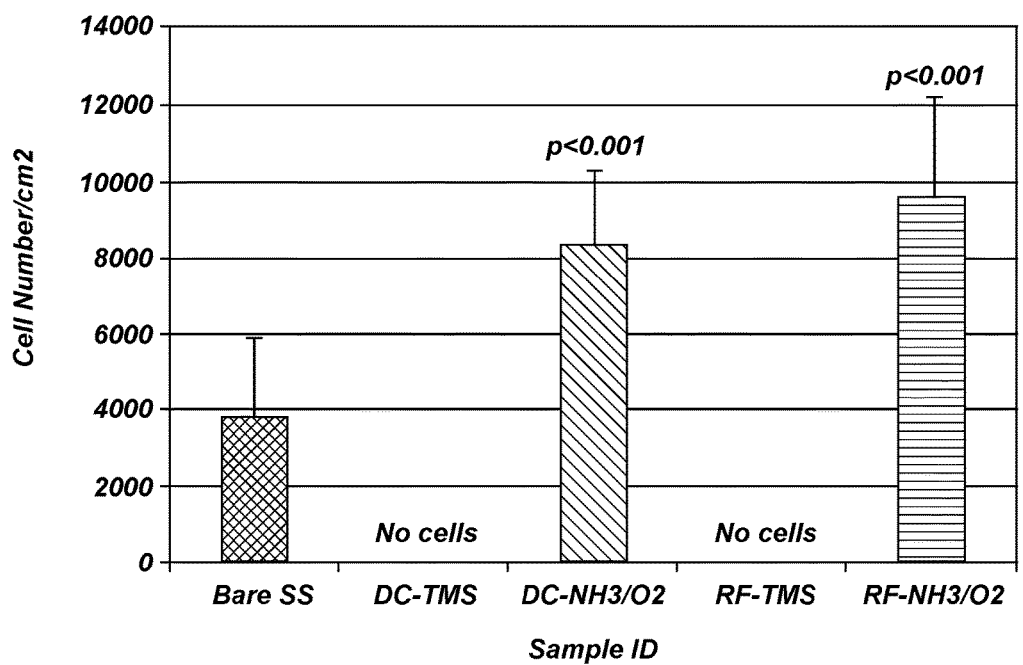
FIG. 2 Numbers of porcine endothelial cells on SS wafers at day 3 post cell seeding vs. types of samples. See FIG. 1 caption for notes to sample ID. In each case, the sample population n=3. Statistical significance indicated on the graph was plasma treatment relative to untreated control (Bare SS), paired t-test.

Endothelial recovery is an essential component for vascular healing by providing critical structural and anti-thrombogenic functions [Chin-Quee et al. *Biomaterials*, 31(4): 648-657, 2010]. Porcine coronary artery endothelial cells (EC), manufactured by Genlantis (San Diego, Calif.), were used for the evaluation of endothelialization. The culture test was first performed on SS wafers at one week after plasma coating following a standard protocol. The results shown in FIG. 2 indicate that there were no cells observed on SS wafers coated with TMS alone in both DC and RF cases. The TMS coating followed by $NH_3/O_2$ plasma surface modification with DC and RF resulted in a 2.2 to 2.5 fold increase in endothelial cell adhesion/growth after 3 days of culture as compared to bare SS.

Figure 3:
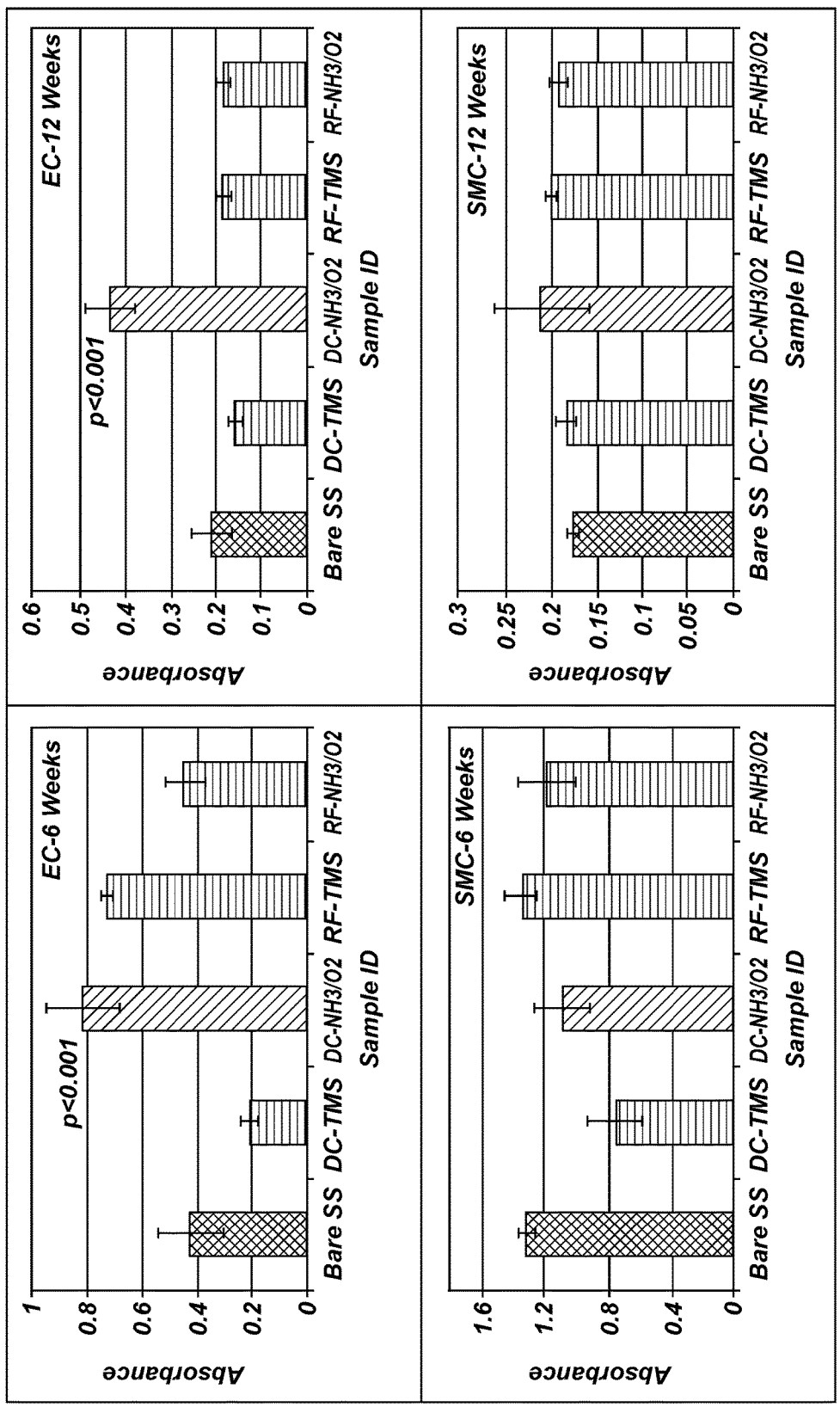
FIG. 3 Numbers of human coronary artery vascular smooth muscle cells on SS wafers at day 1 post cell seeding vs. types of samples. See FIG. 1 caption for notes to sample ID. In each case, the sample population n=2.

To further evaluate the durability of bioactivity created on plasma coated surfaces, cell culture tests were performed on coated SS wafers at 6 and 12 weeks after plasma coatings. Samples were stored in plastic petri dish with covered lid at room temperature. A standard MTT assay [Liu et al. *J. Biomed Mater Res Å*, 78 A (4): 798-807, 2006] was chosen to evaluate the cell vitality on wafers at 3 days post cell seeding. The cell culture results (FIG. 3) indicated that as compared to bare SS, the attachment and growth of EC on DC-$NH_3/O_2$ coated SS wafers were significantly enhanced (2-fold increase) even at 6 and 12 weeks after the plasma coating process. Meanwhile, there was no promotion in growth of porcine coronary artery smooth muscle cells (SMC) on DC-$NH_3/O_2$ coated surfaces observed at both 6 and 12 weeks. These data strongly suggest that a long lasting surface bioactivity enhancing endothelialization can be generated on stents by the invented plasma coatings.

Example 6: Human Coronary Artery Vascular Smooth Cell (VSMC) Attachment

Figure 4:
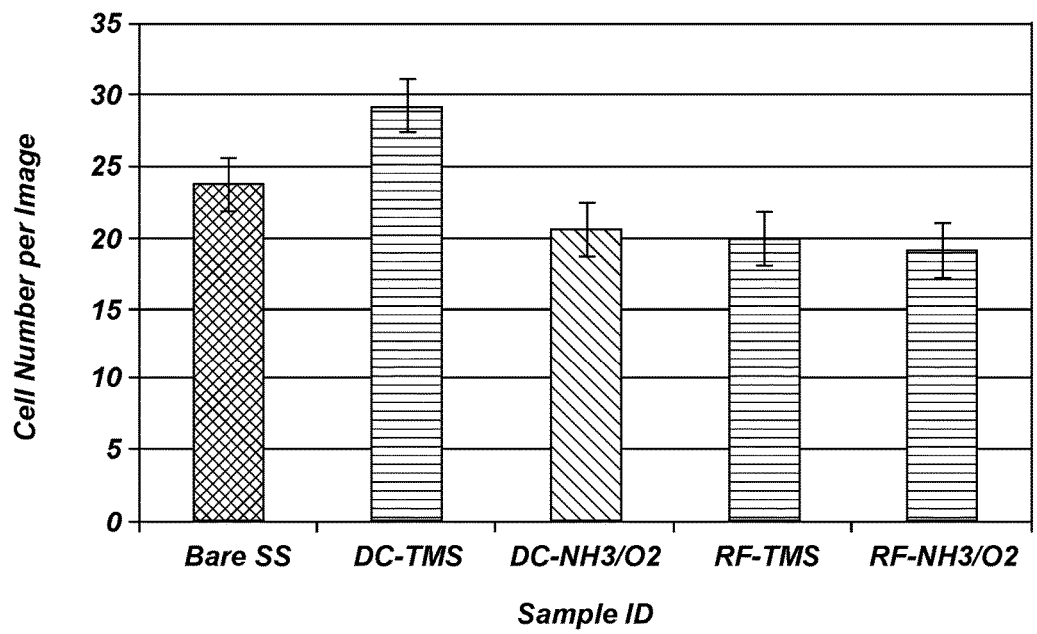
FIG. 4 Attachment/growth of endothelial cells (EC) and smooth muscle cells (SMC) on SS wafers at day 3 post cell seeding vs. types of samples aged at 6 & 12 weeks. See FIG. 1 caption for notes to sample ID. In each case, the sample population n=4. Statistical significance indicated on the graph was plasma treatment relative to untreated control (Bare SS), paired t-test.

Stainless steel wafers with and without plasma coatings or treatment were sterilized by UV light for 2 hours on each side, then placed in a 24 well plate using 2 wafers from each of the 5 groups. 50,000 human coronary artery VSMCs (Catalog Number: C-017-5C, Invitrogen, Carlsbad, Calif.) were then seeded into each well containing one wafer and let grow for 1 day. Then those wafers with cells were fixed in 3% gluteraldehyde, and stained with toludine blue, and rinsed. After rinsing to remove unbound stain, the wafers were then examined by epifluorescence and digitally photographed. The number of cells on each micrograph field was then counted. FIG. 4 indicates that the plasma coated wafers with DC-$NH_3/O_2$ or RF-$NH_3/O_2$ resulted in lower smooth muscle cell attachment than bare stainless steel wafers

Example 7: Inhibition of Restenosis in Animal Studies

Figure 5:
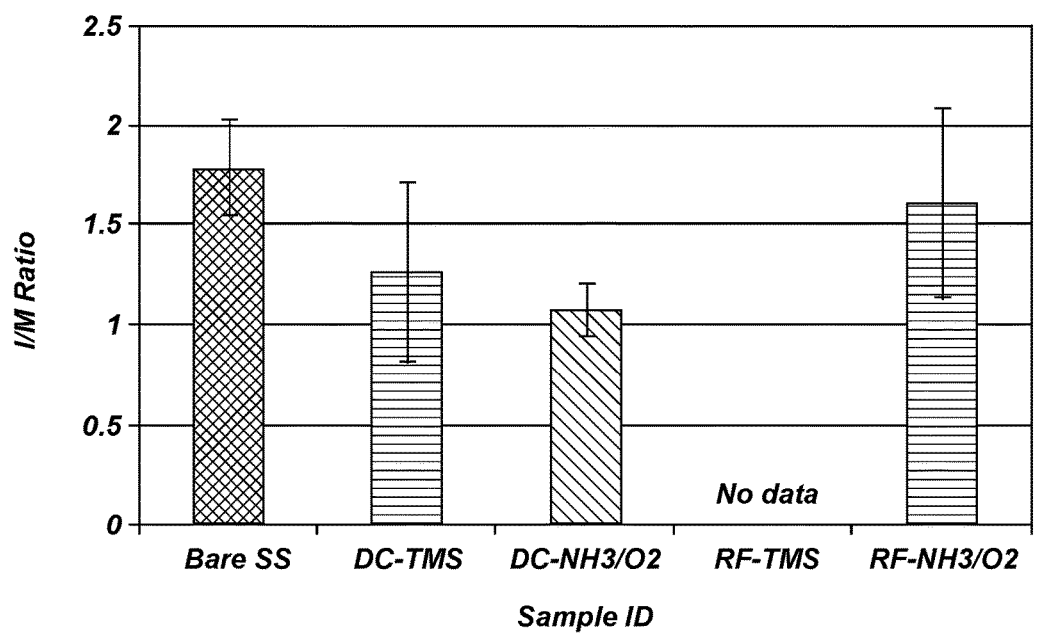
FIG. 5 I/M (intimal area over media area) ratio of stented segments of porcine coronary arteries after 21 days stent implantation. Bare metal stent (BMS) was used as control. See FIG. 1 caption for notes to sample ID.

Large animal trials using swine were performed for stent implantation into swine coronary arteries following the same stent placement procedure as previous [Tharp et al. *Arterioscler Thromb Vasc Biol*, 28(6): 1084-1089, 2008] to further evaluate the performance of plasma coated stents. Histology analysis was made at an end-point of 21 days on stented segments at three sections (proximal, middle, and distal) in the animal studies. Stent sectioning was carried out at HSRL Pathology (Mt. Jackson, Va.). Analysis was performed independently by two blinded investigators using Image J software (Scion Image). Vessel area was measured as the area defined by the external elastic lamina (EEL). Neointimal (NI) area was calculated (vessel area—lumen area—medial area). The ratio of intimal area over media area (I/M) of stented segments was shown in FIG. 5. The DC-$NH_3/O_2$ coated stent (TMS coating followed by $NH_3/O_2$ plasma surface modification with DC plasma) is significantly better than the BMS control in suppressing coronary restenosis ($p<0.001$ in paired t-Test based on 3 stent sections of one stent), suggesting its great promise of inhibiting smooth muscle proliferation and thus limiting in-stent restenosis.

In summary, this invention provides a very different approach to solve the biocompatibility problems with stents by offering great potential to reduce the risk of restenosis and inhibit late stent thrombosis simultaneously. Specifically, our unique two-step plasma coating approach features in: 1) the 1st step of the plasma deposition process, using a silicon-containing monomer creates a uniform and conformal nano-scale plasma coating that not only has tenacious adhesion through the strongest covalent bonding to stent surfaces but also provides a coating surface chemistry being suitable for new functional groups to attach; 2) the 2nd step of plasma treatment using an $NH_3/O_2$ gas mixture will create the desired oxynitrite functional groups with a maximized amount attached onto the plasma coating surface, also through covalent bonding; and 3) combination of the two-steps will thus provide a stable and durable functionalized surface and consequently result in significantly improved performance of the plasma coated coronary stents. As demonstrated in the embodiments, this two-step plasma coating approach has shown great promise in improving the long term biocompatibility of stents, which includes significantly increased endothelialization, durable surface bioactivity, and substantially less restenoisis.

Although the invention has been described in detail with particular reference to these preferred embodiments, other embodiments can achieve the same results. The entire disclosures of all references, applications, patents, and publications cited above, and of the corresponding applications, are hereby incorporated by reference. It is to be understood that the above-described embodiments are only illustrative of application of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

What is claimed is:

1. A method of making a medical device adapted for implantation into a human or animal host wherein the medical device comprises at least one contacting surface for contacting a bodily fluid or tissue, the method comprising:
   (a) depositing a plasma coating of less than 100 nm thickness on the at least one contacting surface using a silicon-containing monomer selected from trimethylsilane (TMS), vinyltrichlorosilane, tetraethoxysilane, vinyltriethoxysilane, hexamethyldisilazane, tetramethylsilane, vinyldimethylethoxysilane, vinyltrimethoxysilane, tetravinylsilane, vinyltriacetoxysilane, or methyltrimethoxysilane to produce a plasma surface; and (b) covalently bonding nitric oxide functional groups to the plasma surface using a plasma comprising a mixture of nitrogen-containing and oxygen-containing molecules.

2. The method of claim 1 wherein the nitrogen-containing molecules each comprise no more than six atoms.

3. The method of claim 1 wherein the nitrogen-containing molecules each comprise no more than four atoms.

4. The method of claim 1 wherein the nitrogen-containing molecules comprise $NH_3$, $NH_4$, $N_2O$, $NO$, $NO_2$, or $N_2O_4$.

5. The method of claim 1 wherein the oxygen-containing molecules comprise $O_2$ or $O_3$.

6. The method of claim 1 wherein the medical device is a stent and wherein the at least one contacting surface comprises the lumen of the stent.

7. The method of claim 1 wherein the silicon-containing monomer is $(CH_3)_3$—SiH.

8. The method of claim 1 wherein the medical device is selected from stents, catheters, balloons, shunts, grafts, valves, pacemakers, pulsed generators, cardiac defibrillators, spinal stimulators, brain stimulators, leads, screws, and sensors.

9. A method of making a medical device adapted for implantation into a human or animal host wherein the medical device comprises at least one contacting surface for contacting a bodily fluid or tissue, the method comprising:
(a) depositing a first plasma coating of less than 100 nm thickness on the contacting surface using a silicon-containing monomer selected from trimethylsilane (TMS), vinyltrichlorosilane, tetraethoxysilane, vinyltriethoxysilane, hexamethyldisilazane, tetramethylsilane, vinyldimethylethoxysilane, vinyltrimethoxysilane, tetravinylsilane, vinyltriacetoxysilane, or methyltrimethoxysilane to produce a first plasma surface; and
(b) depositing a second plasma coating on the first plasma coating using a mixture of nitrogen-containing and oxygen-containing molecules, thereby covalently bonding nitric oxide functional groups to the first plasma surface and resulting in a plasma-modified contacting surface.

10. The method of claim 9, wherein the plasma-modified contacting surface exhibits increased adhesion of at least some mammalian cells compared to a similar contacting surface that is not plasma-modified.

11. The method of claim 9, wherein the plasma-modified contacting surface exhibits decreased restenosis subsequent to placement in blood vessel compared to a similar stent that is not plasma-modified.

12. The method of claim 9, wherein the medical device is a stent and wherein the at least one contacting surface comprises the lumen of the stent.

13. The method of claim 9, wherein the first plasma coating thickness is less than 60 nm.

14. The method of claim 9, wherein the first plasma coating thickness is less than 20 nm.

15. The method of claim 9, wherein the first plasma coating thickness is between 10 and 20 nm.

16. The method of claim 9, wherein the first plasma coating is deposited in less than about 10 minutes.

17. The method of claim 9, wherein the silicon-containing monomer is trimethylsilane (TMS).

18. The method of claim 9, wherein the plasma is fabricated by a glow discharge plasma deposition process.

19. The method of claim 9, wherein the contacting surface is a metallic or polymeric surface.

20. The method of claim 9, wherein the medical device is selected from stents, catheters, balloons, shunts, grafts, valves, pacemakers, pulsed generators, cardiac defibrillators, spinal stimulators, brain stimulators, leads, screws, and sensors.

* * * * *